United States Patent
Karbassi et al.

(10) Patent No.: US 10,762,981 B2
(45) Date of Patent: Sep. 1, 2020

(54) PATHOGENICITY SCORING SYSTEM FOR HUMAN CLINICAL GENETICS

(71) Applicant: Athena Diagnostics, Inc., Marlborough, MA (US)

(72) Inventors: Izabela Karbassi, San Juan Capistrano, CA (US); Christopher Elzinga, San Juan Capistrano, CA (US); Glenn Maston, San Juan Capistrano, CA (US); Joseph Higgins, San Juan Capistrano, CA (US); Sat Dev Batish, San Juan Capistrano, CA (US); Christina Divincenzo, San Juan Capistrano, CA (US); Michele McCarthy, San Juan Capistrano, CA (US); Jennifer Lapierre, San Juan Capistrano, CA (US); Felicita Dubois, San Juan Capistrano, CA (US); Katelyn Medeiros, San Juan Capistrano, CA (US); Jeffery Jones, San Juan Capistrano, CA (US); Corey Braastad, San Juan Capistrano, CA (US)

(73) Assignee: ATHENA DIAGNOSTICS, INC., Marlborough, MA (US)

( * ) Notice: Subject to any disclaimer, the term of this patent is extended or adjusted under 35 U.S.C. 154(b) by 1011 days.

(21) Appl. No.: 15/028,190

(22) PCT Filed: Oct. 22, 2014

(86) PCT No.: PCT/US2014/061730
§ 371 (c)(1),
(2) Date: Apr. 8, 2016

(87) PCT Pub. No.: WO2015/061422
PCT Pub. Date: Apr. 30, 2015

(65) Prior Publication Data
US 2016/0253452 A1    Sep. 1, 2016

Related U.S. Application Data

(60) Provisional application No. 61/894,380, filed on Oct. 22, 2013.

(51) Int. Cl.
*G16B 20/00* (2019.01)
(52) U.S. Cl.
CPC .................. *G16B 20/00* (2019.02)
(58) Field of Classification Search
None
See application file for complete search history.

(56) References Cited

U.S. PATENT DOCUMENTS

| 2005/0193396 A1* | 9/2005 | Stafford-Fraser ..... G06F 3/1438 719/328 |
| 2013/0013213 A1 | 1/2013 | Worthey et al. |
| 2013/0268290 A1 | 10/2013 | Jackson et al. |
| 2014/0278135 A1 | 9/2014 | Pruss et al. |

FOREIGN PATENT DOCUMENTS

| WO | WO 2012/155148 A2 | 11/2012 |
| WO | WO 2013/067001 A1 | 5/2013 |

OTHER PUBLICATIONS

Goldgar et al. Integrated Evaluation of DNA Sequence Variants of Unknown Clinical Significance: Application to BRCA1 and BRCA2 American Journal of Human Genetics vol. 75, pp. 535-544 (Year: 2004).*
Ng et al. SIFT: predicting amino acid changes that affect protein function Nucleic Acids Research vol. 31, pp. 3812-3814 (Year: 2003).*
Ramensky et al. Human non-synonymous SNPs: server and survey Nucleic Acids Research vol. 30 pp. 3894-3900 (Year: 2002).*
Myles et al. An introduction to decision tree modeling Journal of Chemometrics vol. 18, pp. 275-285 (Year: 2004).*
International Preliminary Report on Patentability issued in related International Patent Application No. PCT/US2014/061730, dated Apr. 26, 2016.
Easton et al., "A Systematic Genetic Assessment of 1,433 Sequence Variants of Unknown Clinical Significance in the BRCA1 and BRCA2 Breast Cancer-Predisposition Genes," *American Journal of Human Genetics*, vol. 81, No. 5, pp. 873-883 (2007).
Pastrello et al., "Integrated Analysis of Unclassified Variants in Mismatch Repair Genes," *Genetics in Medicine*, vol. 13, No. 2, pp. 115-124 (2011).
Ohanian et al., "Heuristic Methods for Finding Pathogenic Variants in Gene Coding Sequences," *Journal of the American Heart Association*, vol. 1, No. 5, pp. e002642-e002642 (2012).
Karbassi et al., "A Standardized DNA Variant Scoring System for Pathogenicity Assessments in Mendalian Disorders," *Human Mutations*, vol. 37, No. 1, pp. 127-134 (2015).
European Extended Search Report issued in related European Patent Application No. 14855265.6 dated Dec. 22, 2016.
International Search Report and Written Opinion issued in related International Patent Application No. PCT/US2014/061730, dated Feb. 5, 2015.

(Continued)

*Primary Examiner* — John S Brusca
(74) *Attorney, Agent, or Firm* — Foley & Lardner LLP

(57) ABSTRACT

Provided are methods and systems for determining the clinical significance of a genetic variant. The methods entail determining, for the variant, (a) a function score based on known impact of the variant on a biological function of a cell or protein, (b) a frequency score based on the frequency of the variant in a population, (c) a co-occurrence score based on how the variant co-occurs with a reference variant having known clinical significance relating to a clinical disease or condition, and (d) a family segregation score based on how the variant segregates with a disease or condition in a family; and aggregating, on a computer, the function score, the frequency score, the co-occurrence score, the family segregation score to generate a clinical significance score indicating the clinical significance of the genetic variant.

13 Claims, 8 Drawing Sheets

(56) References Cited

OTHER PUBLICATIONS

Macintyre et al., "Associating disease-related genetic variants in intergenic regions to the genes they impact," *Peer J.* pp. 1-24 (2014).

* cited by examiner

PATHOGENICITY SCORING SYSTEM FOR HUMAN CLINICAL GENETICS

CROSS-REFERENCE TO RELATED APPLICATION(S)

This application is the National Phase of International Patent Application No. PCT/US2014/061730, filed Oct. 22, 2014, which claims priority from U.S. Provisional Patent Application No. 61/894,380, filed Oct. 22, 2013. The contents of these applications are incorporated herein by reference in their entirety.

BACKGROUND

When a DNA sequence variant is identified in a clinical lab, its clinical significance needs be evaluated and appropriately reported. Currently, a static mutation list is assembled at time of discovery of the variant, which is not easy to update in real time. Therefore, variants of unknown clinical significance (VUS) are not routinely evaluated for pathogenicity.

SUMMARY

The present disclosure provides a custom database for the collection and curation of variant-related data. The database not only includes curation of the variants, such as the variants' potential biological functions, but also includes information about individuals having the variant. Such information includes, without limitation, known or projected impact of the variant on a biological function of a cell or protein, the frequency of the variant in a population, co-occurrence of the variant with a reference variant relating to a clinical disease or condition, and/or occurrences of the variant in a family and segregation between the variant and a disease or condition. By including such information in an integrated database, the present technology is able to determine the likely clinical significance of a variant of unknown clinical significance (VUS).

Further, a scoring technique is provided for the reproducible assessment of the clinical significance of a VUS using information retrievable from the database. Also provided are custom tools to create standardized or customizable reports for such VUS.

Accordingly, disclosed herein, in some embodiments, is a method for determining the clinical significance of a genetic variant, comprising determining, for the variant, (a) a function score based on known impact of the variant on a biological function of a cell or protein, (b) a frequency score based on the frequency of the variant in a population, (c) a co-occurrence score based on how the variant co-occurs with a reference variant having known clinical significance relating to a clinical disease or condition, and (d) a family segregation score based on how the variant segregates with a disease or condition in a family; and (e) optionally, a minor evidence score based on information from at least one functional impact prediction algorithm, whether the variant occurs within a critical protein domain, whether the variant would alter a post-translational modification, whether other known pathogenic variants occur within the same codon, and whether the variant is known to occur in at least one patient of a disease or condition; and aggregating, on a computer, the function score, the frequency score, the co-occurrence score, and the family segregation score to generate a clinical significance score indicating the clinical significance of the genetic variant. In some embodiments, the method further comprises retrieving, from a database hosted on a computer server, the known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition. In some embodiments, the aggregation comprises summing up the function score, the frequency score, the co-occurrence score, the family segregation score, and the minor evidence score with pre-determined weights. In some embodiments, the aggregation comprises taking the function score, the frequency score, the co-occurrence score, the family segregation score, and the minor evidence score as inputs in a decision tree. In some embodiments, the method further comprises determining a curated clinical significance score, wherein the aggregation further takes the curated clinical significance score as an input to generate the clinical significance score. In some embodiments, the known or projected impact comprises protein activity change or protein expression level change, and wherein a higher impact leads to a higher clinical significance score. In some embodiments, the protein expression level change is caused by a splicing or translation efficiency change due to the genetic variant. In some embodiments, the frequency score comprises frequency of the variant in normal population, and wherein higher frequency leads to a lower clinical significance score. In some embodiments, a higher co-occurrence with the reference variant relating to a clinical disease or condition leads to a lower clinical significance score. In some embodiments, a higher segregation of the variant with a clinical disease or condition in the family leads to a higher clinical significance score. In some embodiments, the function impact prediction algorithm is selected from SIFT (Sorting Intolerant From Tolerant) and PolyPhen (Polymorphism Phenotyping). In some embodiments, the minor evidence score is based on information from at least two functional impact prediction algorithms.

Disclosed herein, in some embodiments, is a method for identifying a potential therapeutic target for treating a disease or condition, comprising querying, with a computer, a database comprising genetic variants of a plurality of individuals, each individual annotated with clinically diagnosed diseases or conditions, wherein at least one variant has unknown clinical significance and at least one reference variant has known clinical significance, and wherein for each variant, the database comprises known impact of the variant on a biological function of a cell or protein, the frequency of the variant in a population, co-occurrence of the variant with the reference variant relating to a clinical disease or condition, and occurrences of the variant in a family and segregation between the variant and a disease or condition; determining a clinical significance score with a method disclosed herein, for at least one variant in the database; and correlating one of the variants to a disease or condition present in the database, thereby identifying the variant as a potential therapeutic target. In some embodiments, a minor evidence score is included in determining the clinical significance score.

Disclosed herein, in some embodiments, is a method for predicting whether an individual is likely to suffer from a disease or condition, comprising querying, with a computer, a database comprising genetic variants of a plurality of individuals, each individual annotated with clinically diagnosed diseases or conditions, wherein at least one variant has unknown clinical significance and at least one reference variant has known clinical significance, and wherein for each variant, the database comprises known impact of the variant on a biological function of a cell or protein, the frequency of the variant in a population, co-occurrence of the variant with the reference variant relating to a clinical disease or condition, and occurrences of the variant in a family and segregation between the variant and a disease or condition; determining a clinical significance score with a method disclosed herein, for at least one variant in the database; correlating one of the variants to a disease or condition present in the database; and identifying an individual possessing the variant as to likely to suffer from the disease or condition. In some embodiments, a minor evidence score is included in determining the clinical significance score.

Further, disclosed herein, in some embodiments, is a system for determining the clinical significance of a genetic variant, comprising a computer comprising: (a) a module configured to generate a function score based on known impact of the variant on a biological function of a cell or protein. (b) a module configured to generate a frequency score based on the frequency of the variant in a population, (c) a module configured to generate a co-occurrence score based on how the variant co-occurs with a reference variant having known clinical significance relating to a clinical disease or condition, (d) a module configured to generate a family segregation score based on how the variant segregates with a disease or condition in a family, (e) optionally a module configured to generate a minor evidence score based on information from at least one functional impact prediction algorithm, whether the variant occurs within a critical protein domain, whether the variant would alter a post-translational modification, whether other known pathogenic variants occur within the same codon, and whether the variant is known to occur in at least one patient of a disease or condition. In some embodiments, the system further comprises a scoring module. In some embodiments, the system further comprises a communications interface configured to receive data inputs. In some embodiments, the system further comprises a display module configured to display a visual representation of the clinical significance of the genetic variant. In some embodiments, the display module is housed within a user device connected to the computer over a network.

Disclosed herein, in some embodiments, is a computer-implemented method for analyzing the clinical significance of a genetic variant, comprising: (a) processing a search query related to the genetic variant, wherein the search query comprises retrieving information from a database comprising genetic variants from a plurality of individuals, each individual annotated with clinically diagnosed diseases or conditions, wherein at least one variant has unknown clinical significance and at least one reference variant has known clinical significance, and wherein for each variant, the database comprises known or projected impact of the variant on a biological function of a cell or protein, the frequency of the variant in a population, co-occurence of the variant with the reference variant relating to a clinical disease or condition, and occurrences of the variant in a family and segregation between the variant and a disease or condition, information from at least one functional impact prediction algorithm, information regarding whether the variant occurs within a critical protein domain, information regarding whether the variant would alter a post-translational modification, information regarding whether other known pathogenic variants occur within the same codon, and information regarding whether the variant is known to occur in at least one patient of a disease or condition, (b) retrieving results of the search query, (c) inferring measured scores based on the results of the search query, (d) aggregating the measured scores, and (e) rendering a visual representation of the aggregation of the measured scores. In some embodiments, the method further comprises sending the visual representation over a network to a user device.

Disclosed herein, in some embodiments, is a visual representation of the clinical significance of a genetic variant, wherein the visual representation displays the results of a method as disclosed herein.

Disclosed herein, in some embodiments, is an article of manufacture, comprising a non-transitory computer-readable medium comprising a non-transitory computer-readable medium comprising computer readable instructions which when executed by a computer, cause the computer to perform a method disclosed herein.

DETAILED DESCRIPTION

Figure 1:
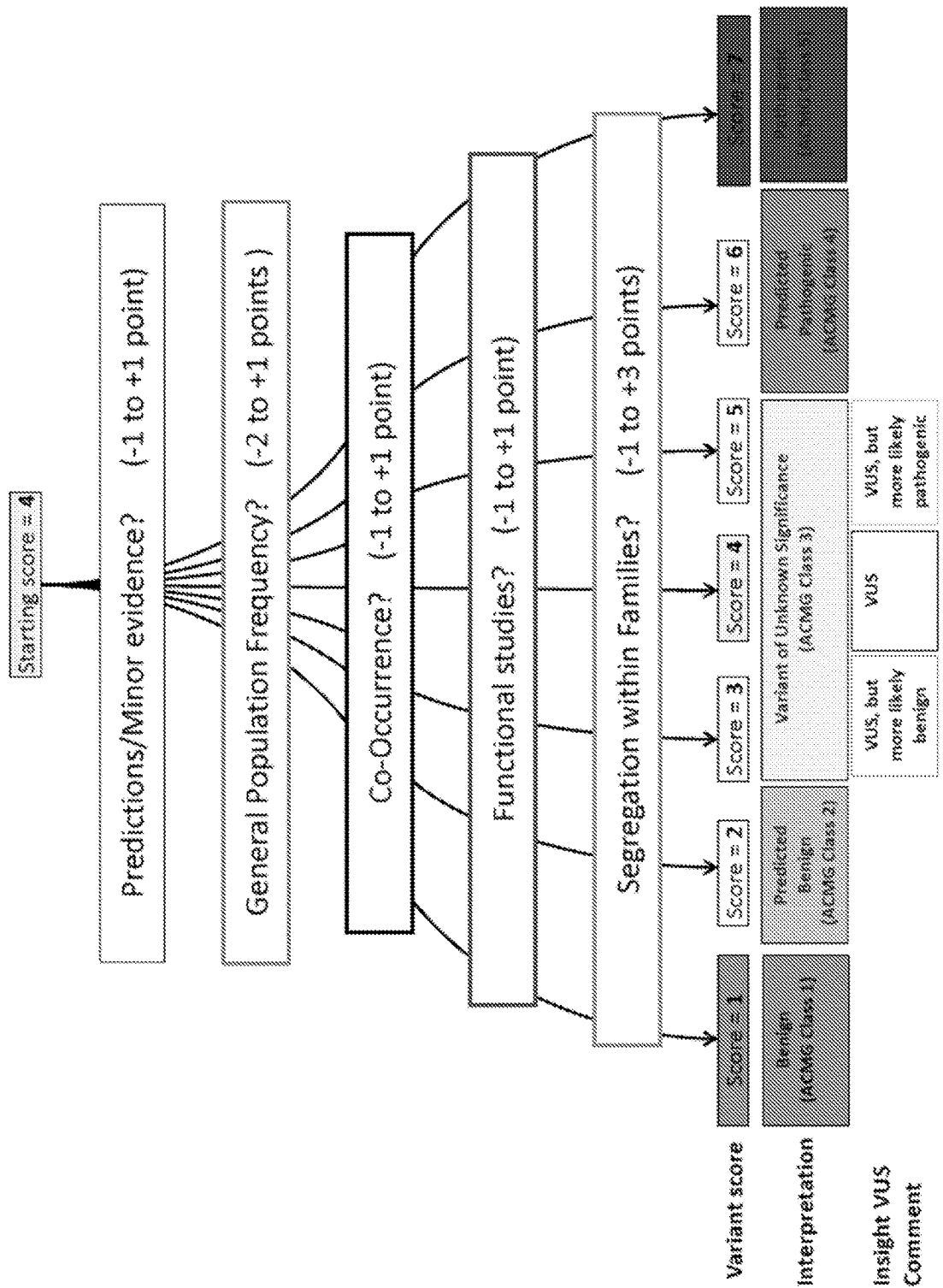
FIG. 1 illustrates an exemplary process for determining a clinical significance score for a variant of unknown clinical significance (VUS).

Provided are methods and systems of assessing and assigning pathogenicity scores to variants and curating mutation lists. Prior to the present disclosure, paper mutation lists were used in the clinical operation which were much less frequently updated after product launch. Additionally, there was little consistency between individuals that assembled the mutation list. As such, a variant assessed might be deemed pathogenic by one, but if assessed by another might be considered a variant of unknown significance. Finally, variants of unknown significance were listed on reports, but offered the physician no guidance as to potential patient impact.

All numerical designations, e.g., pH, temperature, time, concentration, and molecular weight, including ranges, are approximations which are varied (+) or (−) by increments of 0.1, 5% or 10%. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

The term "variant" or "genetic variant" refers to an alternative form of a gene, a genomic sequence, or portions thereof. A variant can also be referred to on a protein or RNA level, corresponding to the genomic change. In some embodiments, a variant causes changes of amino acids in a protein sequence, but can also impact the function or activity of a protein or cell otherwise, such as in terms of RNA splicing, translation, or on other levels of transcription or translation regulation.

A "reference variant" or "mutation" with known clinical significance refers to a variant on which a functional relationship between the variant and a disease or condition has been investigated and validated with supporting data. Such validation, however, does not require regulatory approval or consensus in the clinical community.

LOD stands for "logarithm of the odds." In the field of genetics, the LOD score is a statistical estimate of whether two genes, or a gene and a disease gene, are likely to be located near each other on a chromosome. A LOD score of 3 or higher is generally understood to mean that the odds are a thousand to one that two genes are linked, and therefore inherited together.

Methods of Determining Pathogenicity of a Variant

One embodiment of the present disclosure provides a method for determining the clinical significance of a genetic variant. The method entails, in one aspect, determining, for the variant, (a) a function score based on known impact of the variant on a biological function of a cell or protein, (b) a frequency score based on the frequency of the variant in a population, (c) a co-occurrence score based on how the variant co-occurs with a reference variant having known clinical significance relating to a clinical disease or condition, and/or (d) a family segregation score based on how the variant segregates with a disease or condition in a family and/or e) a minor evidence score, based on information which can include, but is not limited to, information from at least one functional impact prediction algorithm, whether the variant occurs within a critical protein domain, whether the variant would alter a post-translational modification, whether other known pathogenic variants occur within the same codon, and whether the variant is known to occur in at least one patient of a disease or condition; and aggregating, on a computer, the function score, the frequency score, the co-occurrence score, and/or the family segregation score to generate a clinical significance score indicating the clinical significance of the genetic variant. In some embodiments, calculated of at least one of the scores is accomplished by Chi Squared Hypothesis testing.

FIG. 1 illustrates such a method. For a variant of unknown clinical significance (VUS), a starting score of 4 is given; a score of 7 indicates strong clinical significance and 1 indicates weak clinical significance.

In one optional step, a curated clinical significance score is given to the VUS, which score can be provided during curation of the VUS in a database. Such curation can be based on a curator's understanding of the gene function or on experimental evidences.

Figure 2:
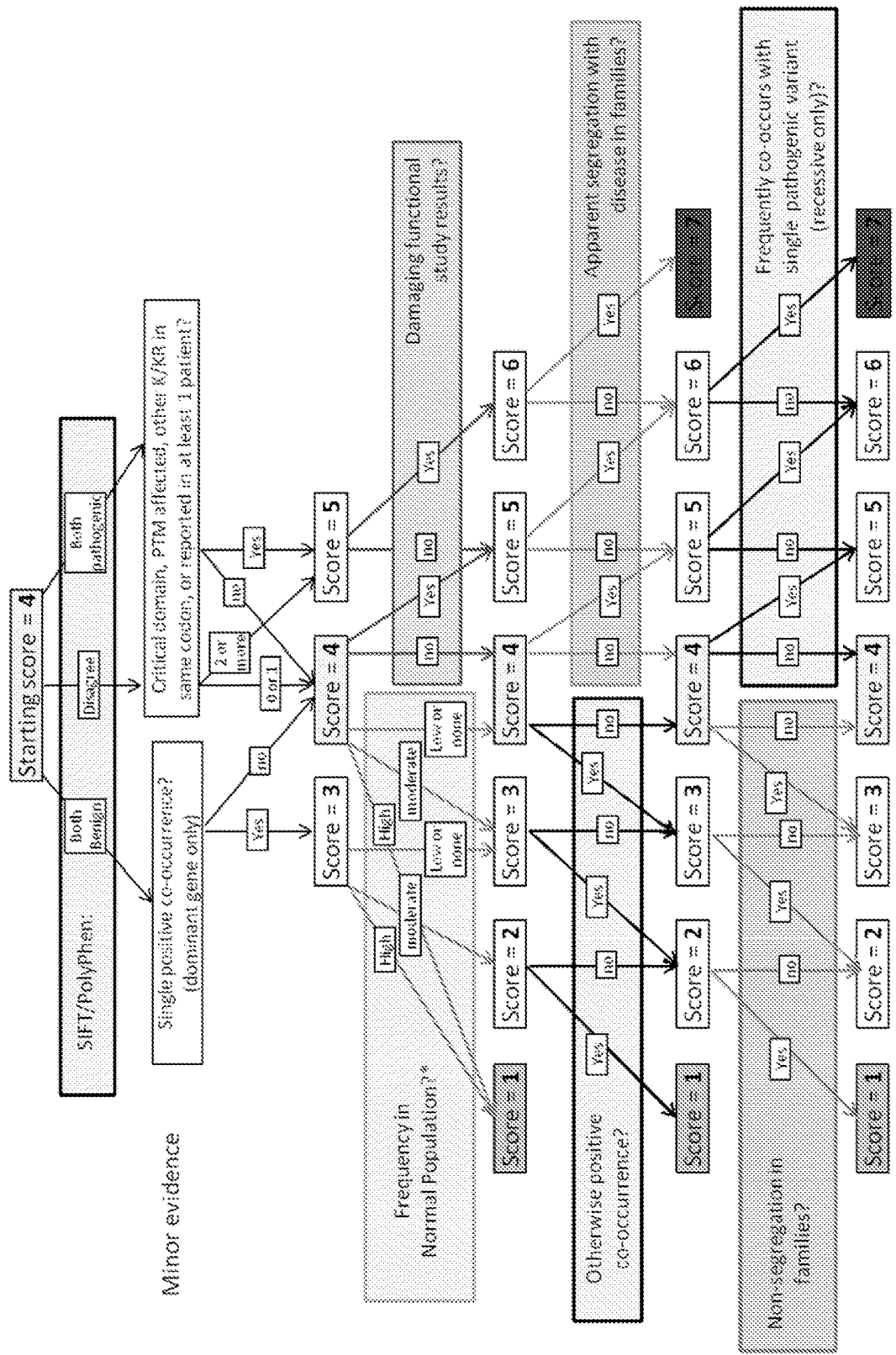
FIG. 2 provides an example for determining a clinical significance score for a VUS that causes change of at least an amino acid in a protein sequence.

FIG. 2 illustrates a process for a variant that causes an amino acid substitution in a protein.

Figure 3:
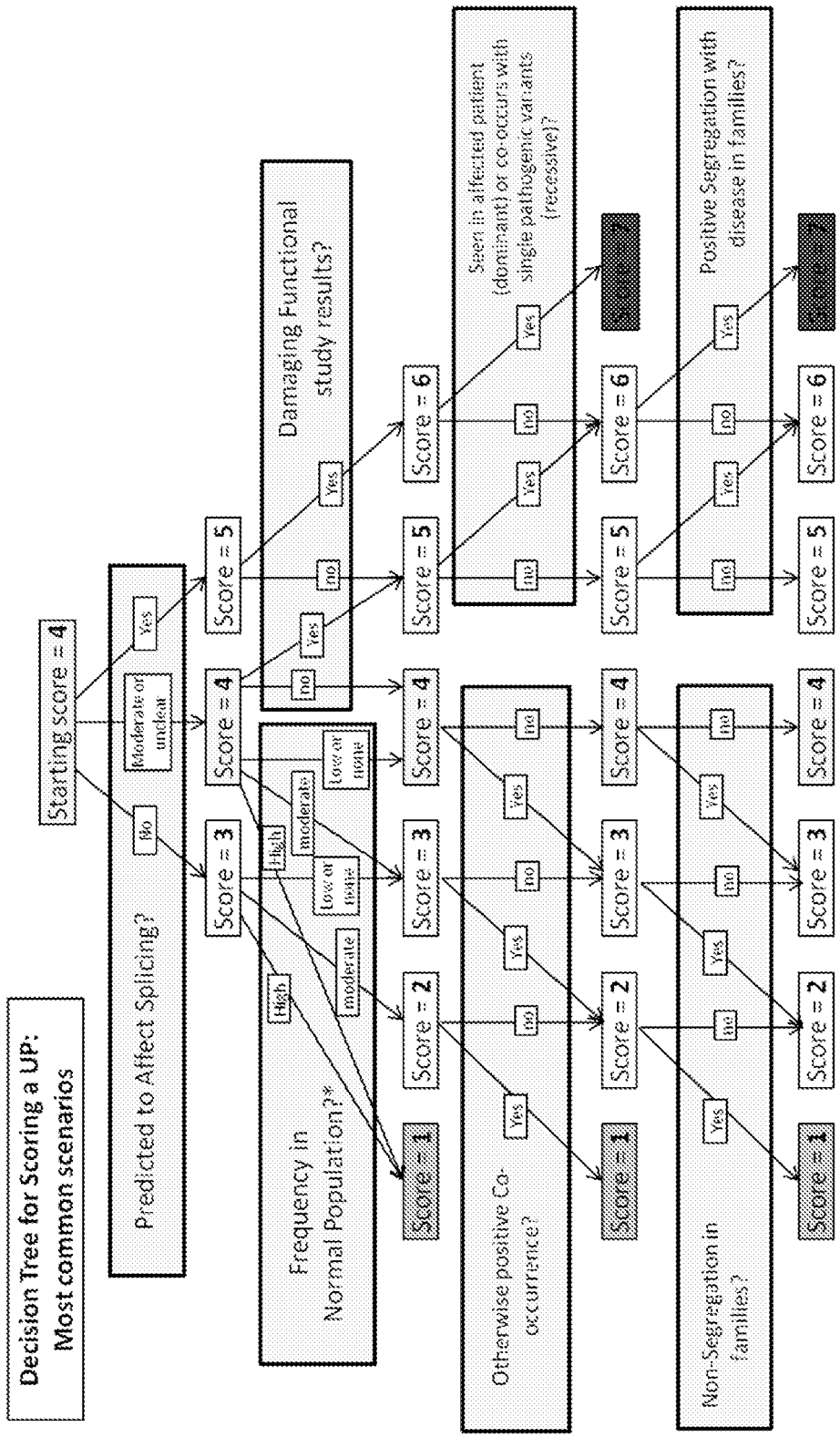
FIG. 3 provides an example for determining a clinical significance score for a VUS that does not change the amino acid sequence of a protein.

FIG. 3, on the other hand, illustrates a process for a variant that does not cause amino acid substitution in a protein, but instead may impact protein or cell function through splicing or translation regulation.

Figure 4:
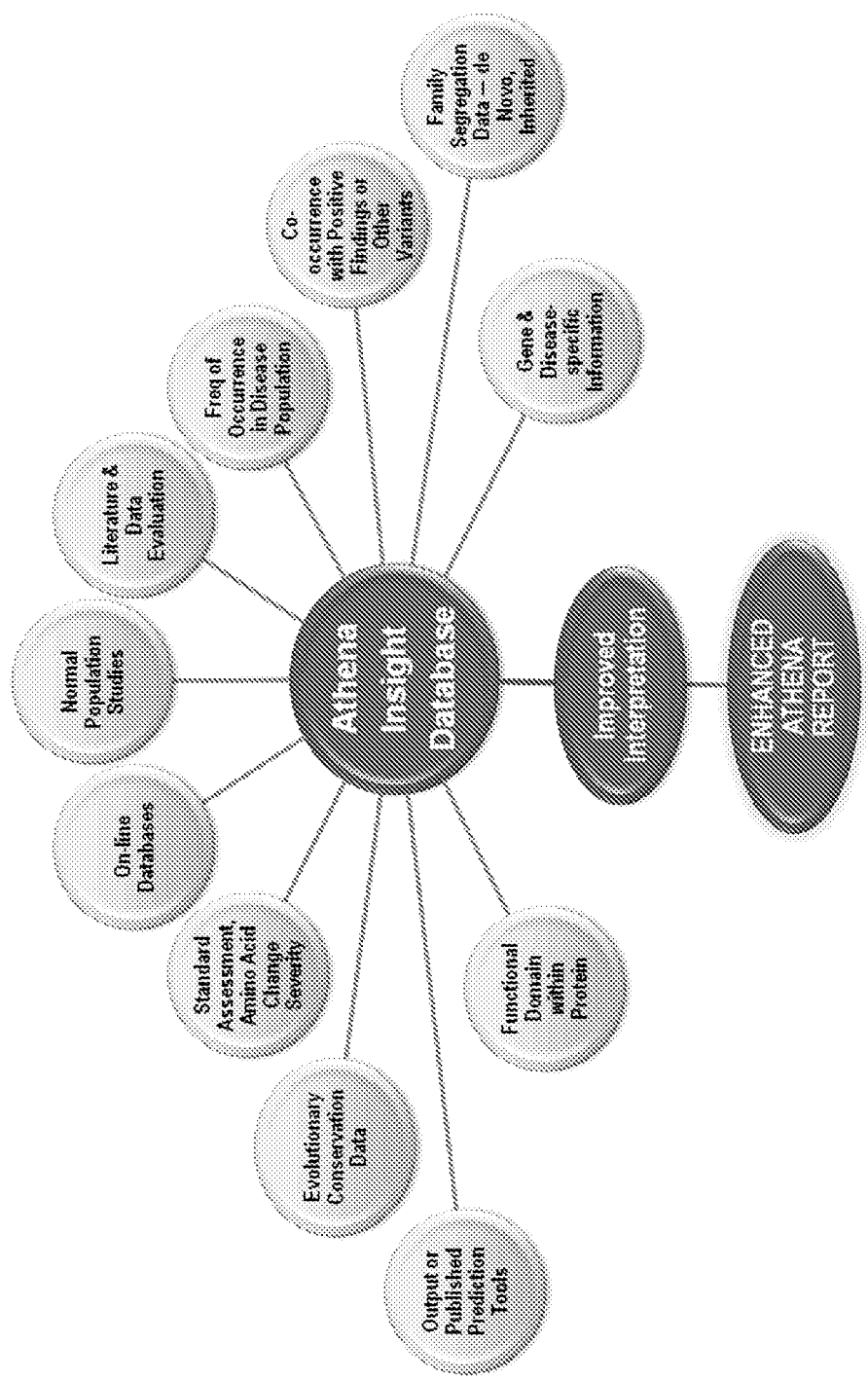
FIG. 4 exemplifies the content of a custom database according to the present disclosure.

In one embodiment, a variant database (as illustrated in FIG. 4) is provided that includes information regarding known or projected impact of a variant on a biological function of a cell or protein, the frequency of the variant in a population, co-occurrence of the variant with a reference variant relating to a clinical disease or condition, and/or occurrences of the variant in a family and segregation between the variant and a disease or condition.

In some aspects, the disclosed method includes generation of at least two, three, four, or five of the scores selected from the function score, the frequency score, the co-occurrence score, the family segregation score, the minor evidence score and/or the curated clinical significance score. In some aspects, at least the co-occurrence score, the family segregation score are generated. In some aspects, the function score is also generated, or the frequency score is also generated.

Once the required scores are generated, they can be aggregated to obtain a clinical significance score. In one embodiment, the aggregation includes summing up the function score, the frequency score, the co-occurrence score, and the family segregation score with pre-determined weights. In one embodiment, the aggregation includes taking the function score, the frequency score, the co-occurrence score, and the family segregation score as inputs in the execution of a decision tree. FIG. 2-3 illustrate such aggregation methods.

In some embodiments, aggregation to obtain a clinical significance score comprises assigning the calculated scores a pre-determined weight. In some embodiments, the predetermined weight assigned to a score is a positive or negative numerical value. In some embodiments, the predetermined weight assigned to a score is a positive or negative integer value. In some embodiments, the predetermined weight assigned to a score is zero.

Function Score

In some aspects, a function score is determined based on known or projected impact of the variant on a biological function of a cell or protein.

For a VUS that causes amino acid changes, the functional impact can be determined or predicted based on the amino acid sequence change. Methods are known in the art to make such determination and prediction.

In some embodiments, determining the function score of a variant comprises determining whether the variant is damaging to protein function. In some embodiments, determining the function score of a variant comprises determining whether a variant has no impact on protein function.

It is contemplated that, in such aspects, the known or projected impact comprises protein activity change or protein expression level change, and wherein a higher impact leads to a higher clinical significance score. In some aspects, the protein expression level change is caused by a splicing or translation efficiency change due to the genetic variant.

In some embodiments, the impact on protein function is directly relevant to the molecular basis of a disease.

In some embodiments, determination of a function score comprises analysis of all functions of a protein that are relevant to a disease.

Frequency Score

Another score that can be generated in this process is a frequency score based on the frequency of the variant in a population.

In some aspects, the frequency score comprises frequency of the variant in normal population, and wherein higher frequency leads to a lower clinical significance score.

It is contemplated that a variant that is more frequently present in normal population, a population without disease or without a particular disease of concern, is less likely to have clinical significance.

In some embodiments, determining the frequency score comprises considering whether the variant frequency in the normal population is greater than ten times higher than the disease allele frequency. In some embodiments, determining the frequency score comprises considering whether the variant frequency in the normal population is greater than two times, five times, twenty times, twenty five times, fifty times, or one hundred times higher than the disease allele frequency.

In some embodiments, determining the frequency score comprises determining whether the variant frequency in the normal population is between 3 times and 10 times above disease allele frequency. In some embodiments, determining the frequency score comprises determining whether the variant frequency is equal up to 3 times higher than the disease allele frequency.

Co-Occurrence Score

Yet another score that can be generated in this process is a co-occurrence score based on how the variant co-occurs with a reference variant having known clinical significance relating to a clinical disease or condition.

In some aspects, a higher co-occurrence with the reference variant relating to a clinical disease or condition leads to a lower clinical significance score.

In some embodiments, co-occurrence of certain clinically-relevant results (especially otherwise positive results) with the reference variant relating to a clinical disease or condition leads to a lower clinical significance score.

In some aspects, the co-occurrence score is obtained by comparing the occurrence of the variant to one, two, three or even more reference variants that correlate with the variant in terms of presence in patients, in particular among patients having the same diseases or conditions. In some aspects, at least one of such reference variants have known clinical significance. For reference variants without known clinical significance, the presently disclosed method can be used to predict its clinical significance.

In some embodiments, determining the co-occurrence score comprises determining whether a nonsynonymous change co-occurs with an otherwise positive result in a single case.

In some embodiments, determining the co-occurrence score comprises determining whether a variant co-occurs with a positive variant in multiple cases.

In some embodiments, determining the co-occurrence score comprises determining whether a variant in a recessive gene co-occurs with one additional known pathogenic variant in multiple cases. In some embodiments, in making such a determination, co-occurrence must occur in at least 3 cases.

In some embodiments, co-occurrence must occur in a statistically significant portion of patients for the variant to be considered more likely to be pathogenic.

In some embodiments, calculation of a co-occurrence score is based on how the variant co-occurs with a combination of reference variants, in the case of recessive diseases or conditions.

In some embodiments, Chi Squared Hypothesis testing is used to determine the co-occurrence score.

Family Segregation Score

Still another score that can be generated in this process is a family segregation score based on how the variant segregates with a disease or condition in a family.

In some aspects, a higher segregation of the variant with a clinical disease or condition in the family leads to a higher clinical significance score.

Both the co-occurrence score and the family segregation score cannot be obtained from a single variant or a single patient, and require a database that integrate variants and patients. This highlights an additional advantage of the present disclosure, which also provides a database of such integrated information.

In some embodiments, determining the family segregation score includes determination of a LOD score. In some embodiments, determining the family segregation score comprises determining whether a LOD score is over 3.0. In some embodiments, determining the family segregation score comprises determining whether a LOD score is over 2.0 but under 3.0. In some embodiments, determining the family segregation score comprises determining whether a LOD score is over 1.0, but under 2.0. In some embodiments, determining the family segregation score comprises determining whether a LOD score is above −1.0, but above −2.0. In some embodiments, determining the family segregation score comprises determining whether a LOD score less than −2.0.

In some embodiments, determining the family segregation score comprises determining whether a variant is de novo, wherein paternity is not confirmed. In some embodiments, determining the family segregation sore comprises determining whether a variant is de novo, wherein paternity is confirmed. In some embodiments, determining the family segregation sore comprises determining whether there are two cases where a variant is de novo, wherein paternity is not confirmed. In some embodiments, determining the family segregation sore comprises determining whether a variant is de novo in two cases, wherein paternity is confirmed. In some embodiments, determining the family segregation score comprises determining whether a variant is de novo in at least three cases, wherein paternity is not confirmed.

In some embodiments, Chi Squared Hypothesis testing is used to determine the family segregation score.

Minor Evidence Score

In some embodiments, a minor evidence score is utilized in determining the clinical significant of a genetic variant.

In some embodiments, the minor evidence score includes information based on prediction algorithms, knowledge regarding the relevant protein domain, whether or not the variant has been reported in a patient, whether other known pathogenic variants occur at the same codon, and splicing predictions.

In some embodiments, the function impact prediction algorithm is selected from SIFT (Sorting Intolerant From Tolerant) and PolyPhen (Polymorphism Phenotyping).

In some embodiments, a functional impact prediction algorithm analyzes a variant for potential effect on post-translational modifications of an encoded protein. An example of such an algorithm can be found online at http://www.cbs.dtu.dk/services/

In some embodiments, the minor evidence score is based on information from at least two functional impact prediction algorithms.

Additional Methods

Also provided, in one embodiment, is a method for identifying a potential therapeutic target for treating a disease or condition. In one embodiment, the method entails querying, with a computer, a database comprising genetic variants of a plurality of individuals, each individual annotated with clinically diagnosed diseases or conditions, wherein at least one variant has unknown clinical significance and at least one reference variant has known clinical significance, and wherein for each variant, the database comprises known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition; determining a clinical significance score with a method of the present disclosure, for at least one variant in the database; and correlating one of the variants to a disease or condition present in the database, thereby identifying the variant as a potential therapeutic target. In some embodiments, a minor evidence score is included in determining the clinical significance score.

Such a method demonstrates the technical advancement provided by the present technology, both in terms of its ability to predict the clinical significance of a particular variant and identify a variant, among many variants in a variant database, as a potential therapeutic target. Once the target is identified, additional pharmaceutical research can be carried out to identify pharmaceutical agents to target (e.g., activate, deactivate, or alter) the potential therapeutic target, to achieve a therapeutic purpose.

Also provided, in yet another embodiment, is a method for predicting whether an individual is likely to suffer from a disease or condition. The method entails, in some aspects, querying, with a computer, a database comprising genetic variants of a plurality of individuals, each individual annotated with clinically diagnosed diseases or conditions, wherein at least one variant has unknown clinical significance, the database comprises known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition; determining a clinical significance score with a method of the present disclosure, for at least one variant in the database; correlating one of the variants to a disease or condition present in the database; and identifying an individual possessing the variant as to likely to suffer from the disease or condition. In some embodiments, the database comprises at least one reference variant having known clinical significance. In some embodiments, a minor evidence score is included in determining the clinical significance score. The method can also include generating a report including relevant scores and prediction methods and processes.

Computer Implementation

The methodology described here can be implemented on a computer system or network.

Accordingly, disclosed herein, in some embodiments, is a system for determining the clinical significance of a genetic variant, comprising a computer comprising: (a) a module configured to generate a function score based on known impact of the variant on a biological function of a cell or protein, (b) a module configured to generate a frequency score based on the frequency of the variant in a population, (c) a module configured to generate a co-occurrence score based on how the variant co-occurs with a reference variant or variants having known clinical significance relating to a clinical disease or condition, (d) a module configured to generate a family segregation score based on how the variant segregates with a disease or condition in a family, (e) optionally a module configured to generate a minor evidence score based on information from at least one functional impact prediction algorithm, whether the variant occurs within a critical protein domain, whether the variant would alter a post-translational modification, whether other known pathogenic variants occur within the same codon, and whether the variant is known to occur in at least one patient of a disease or condition. In some embodiments, the system further comprises a scoring module. In some embodiments, the system further comprises a communications interface configured to receive data inputs. In some embodiments, the system further comprises a display module configured to display a visual representation of the clinical significance of the genetic variant. In some embodiments, the display module is housed within a user device connected to the computer over a network. In some embodiments, a module configured to generate a co-occurrence score is based on how the variant co-occurs with a combination of reference variants, in the case of recessive diseases or conditions. In some embodiments, the computer comprises at least one module configured to perform Chi Squared Hypothesis Testing. In some embodiments, the module configured to generate a co-occurrence score is configured to perform Chi Squared Hypothesis Testing. In some embodiments, the module configured to generate a family segregation score is configured to perform Chi Squared Hypothesis Testing. In some embodiments, one or more of the modules is configured to query a database to search for relevant published literature. In some embodiments, one or more of the modules is configured to query a gene-specific Leiden Open Variation Database (LOVD). In some embodiments, one or more of the modules is configured to query an independent database related to the gene of interest.

Further disclosed herein, in some embodiments, is a computer-implemented method for analyzing the clinical significance of a genetic variant, comprising: (a) processing a search query related to the genetic variant, wherein the search query comprises retrieving information from a database comprising genetic variants from a plurality of individuals, each individual annotated with clinically diagnosed diseases or conditions, wherein at least one variant has unknown clinical significance, and wherein for each variant, the database comprises known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition, information from at least one functional impact prediction algorithm, information regarding whether the variant occurs within a critical protein domain, information regarding whether the variant would alter a post-translational modification, information regarding whether other known pathogenic variants occur within the same codon, and information regarding whether the variant is known to occur in at least one patient of a disease or condition, (b) retrieving results of the search query, (c) inferring measured scores based on the results of the search query, (d) aggregating the measured scores, and (e) rendering a visual representation of the aggregation of the measured scores. In some embodiments, the database comprises information regarding at least one reference variant having known clinical significance. In some embodiments, the method further comprises sending the visual representation over a network to a user device.

In some embodiments, a database disclosed herein comprises information relevant to calculating one or more of the function score, the frequency score, the co-occurrence score, the family segregation score, and the minor evidence score. In some embodiments, the database comprises published literature relevant to a particular variant or gene. In some embodiments, the database is a gene-specific Leiden Open Variation Database (LOVD). In some embodiments, the database is an independent database related to the gene or variant of interest. In some embodiments, the database disclosed herein is housed on a SQL server. In some embodiments, the database is housed on Microsoft Access software.

In some embodiments, the database is housed on a spreadsheet software. In some embodiments, the spreadsheet software comprises calculation tools and a macro programming language. In some embodiments, the macro programming language is Visual Basic for Applications.

Also disclosed herein, in some embodiments, is an article of manufacture, comprising a non-transitory computer-readable medium comprising a non-transitory computer-readable medium comprising computer readable instructions which when executed by a computer, cause the computer to perform a method disclosed herein. In some embodiments, disclosed herein is an article of manufacture comprising a non-transitory computer readable storage medium to tangibly store instructions for performing the methods disclosed herein, which, when executed, cause one or more computers in a network of computer to: receive a request for displaying a report on a portable computing device, display a report displaying a visible representation of the clinical significance of a genetic variant.

In some embodiments, a suitable computer system can include at least a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by, but are not limited to, central processing units, microprocessors, graphics processing units, physics processing units, digital signal processors, network processors, front end processors, coprocessors, data processors and audio processors. The term "memory" connotes an electrical device that stores data for retrieval. In one aspect, therefore, a suitable memory is a computer unit that preserves data and assists computation. More generally, suitable methods and devices for providing the requisite network data transmission are known.

Also contemplated is a non-transitory computer readable medium that includes executable code for carrying out the described methodology. In certain embodiments, the medium further contains data or databases needed for such methodology.

Information stored in or maintained in the one or more databases may be provided in conformance with a database system format such as, but not limited to, the Structured Query Language (SQL) format. Database query and access instructions, for example, in the form of one or more scripts, may be used which, when executed by a processor, serve to access, store and retrieve data maintained in the one or more databases according to the instructions contained in the script.

The system may comprise application software instructions which may implement a user interface portion for generating interactive pages or display screens by which a user/participant may provide data to and receive information from the system and the database using a human-machine interface. In embodiments, interactive pages may include user dialog boxes for accepting user entered information. The human-machine interface may comprise a Graphical User Interface (GUI) portion for prompting the user to enter data by providing an interactive dialog box or message box instructing the user to enter particular data, or to select from among a multitude of options provided using a pull-down menu. In embodiments, a user may interact with the system via the graphical user interface by using a pointing device and/or other data entry device. The GUI portion may place the output of the system in a format for presentation to a user via the display. In embodiments, the GUI may be implemented as a sequence of Java instructions.

In embodiments of the present invention, the various program operations as described herein may be provided by the system in response to the one or more processors executing one or more sequences of computer-readable instructions contained in main memory. Such instructions may be read into main memory from another computer-readable medium. Execution of the sequences of instructions contained in main memory may cause one or more processors of the system to perform the process steps described herein. It should be appreciated that embodiments of the system may perform fewer or additional processes as compared to those described herein. As noted, the one or more processors may be arranged in a multi-processing arrangement. In embodiments, hard-wired circuitry may be used in place of or in combination with software instructions to implement the invention. Thus, embodiments of the invention are not limited to any specific combination of hardware circuitry and software.

Embodiments can include program products comprising non-transitory machine-readable storage media for carrying or having machine-executable instructions or data structures stored thereon. Such machine-readable media may be any available media that may be accessed by a general purpose or special purpose computer or other machine with a processor. By way of example, such machine-readable storage media may comprise RAM, ROM, EPROM, EEPROM, CD-ROM or other optical disk storage, magnetic disk storage or other magnetic storage devices, or any other medium which may be used to store desired program code in the form of machine-executable instructions or data structures and which may be accessed by a general purpose or special purpose computer or other machine with a processor. Combinations of the above also come within the scope of "machine-readable media." Machine-executable instructions comprise, for example, instructions and data that cause a general purpose computer, special-purpose computer or special-purpose processing machine(s) to perform a certain function or group of functions.

In another embodiment of the present invention, software is provided that performs the analysis of the clinical significance of a variant. When a subject's genomic sequence is obtained, it may be entered into the software. The software is designed to access a database as described and perform the analysis of the clinical significance of a variant, according to the present invention, outputting the calculated significance score so that a doctor, genetic counsel, other medical professional, or patient may obtain the score, and optionally, a report of the score, as disclosed herein. It is contemplated that the software of the present invention may be software stored on a local computer, or may alternatively be server or web-based, allowing for its access from remote computers.

The system also comprises a communication interface for providing one-way, two-way or multi-way data communication with the network, and/or communication directly with other devices. In embodiments, the communication interface may comprise a modem, a transceiver Integrated Services Digital Network (ISDN) card, a WAN card, an Ethernet interface, or the like, to provide a data communication connection to a corresponding type of communication medium. As another example, the communication interface may comprise a LAN card to provide a data communication connection to a compatible LAN. Wireless links may also be implemented. In such wireless links, the communication interface may communicate with a base station communicatively coupled to a network server. In any such implementation, the communication interface sends and receives electrical, electromagnetic, radio, infrared, laser, or optical signals that carry digital data streams representing various types of information. Any combination of the above interfaces may also be implemented.

In embodiments, the communication interface may be communicatively coupled to a web server configured in the one or more processors to generate and output web content that is suitable for display using a web browser at a computing device. In embodiments, the server may generate and transmit requested information through the communication interface to a requesting terminal via Hypertext Transfer Markup Language (HTML) formatted pages, eXtensible Markup Language (XML) formatted pages, or the like, which may be provided as World Wide Web pages that may enable navigation by hyperlinks. The server program may be used to receive commands and data from clients' terminals, access and process data from various sources, and output computer-executable instructions and data using the network. Interactive pages transmitted and received using the network may conform to necessary protocols.

In embodiments, the web server configured in the one or more processors may correspond to a secure web application server behind a web server program that a service provider employs to run one or more web based application programs in a secure fashion. Such a secure web application server may be configured to execute one or more web based application programs, respond to commands and data received from the clients (via a web page supported by the web server), and provide data and results to the clients. The web server and the web application server may be implemented using a single computing platform. Alternatively, it may also be implemented using multiple separate and distributed computing platforms.

Embodiments of the present invention have been described in the general context of method steps which may be implemented in one embodiment by a program product including machine-executable instructions, such as program code, for example in the form of program modules executed by machines in networked environments. Generally, program modules include routines, programs, logics, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

As previously indicated, embodiments of the present invention may be practiced in a networked environment using logical connections to one or more remote computers having processors. Those skilled in the art will appreciate that such network computing environments may encompass many types of computers, including personal computers, hand-held devices, multi-processor systems, microprocessor-based or programmable consumer electronics, network PCs, minicomputers, mainframe computers, and so on. Embodiments of the invention also may be practiced in distributed and cloud computing environments where tasks are performed by local and remote processing devices that are linked, by hardwired links, by wireless links or by a combination of hardwired or wireless links, through a communications network. In a distributed computing environment, program modules may be located in both local and remote memory storage devices.

In some embodiments, a user device may be any, device, or machine for processing or displaying data, including by way of example a programmable processor, a computer (such as a laptop), a server, a mobile device such as a smart phone or a tablet, a system on a chip, or multiple ones or combinations of the foregoing. In some embodiments, the user device may generally include a browser configured to display webpages.

Embodiments of the invention have been described in the general context of method steps which may be implemented in embodiments by a program product comprising machine-executable instructions, such as program code, for example in the form of program modules executed by machines in networked environments. Generally, program modules include routines, programs, objects, components, data structures, etc., that perform particular tasks or implement particular data types. Multi-threaded applications may be used, for example, based on Java or C++. Machine-executable instructions, associated data structures, and program modules represent examples of program code for executing steps of the methods disclosed herein. The particular sequence of such executable instructions or associated data structures represent examples of corresponding acts for implementing the functions described in such steps.

Reports

In some embodiments, the methods disclosed herein include transformation of the relevant scores into a report.

In some embodiments, the report comprises a visual representation of the calculated clinical significance score. In some embodiments, the visual representation is a spectrum representing the range from benign to pathogenic. In some embodiments, the visual representation is a heat map representing the range from benign to pathogenic. In some embodiments, the visual representation is a visual indicator of the score, wherein the visual indicator is a numerical value, or a letter value. In some embodiments, the visible representation is a color gradient chart, ranging from benign to pathogenic. In some embodiments, the visible representation of the clinical significant is a display of the calculated pathogenicity score, In some embodiments, the display of the calculated pathogenicity score is accompanied by an explanation of the level of pathogenicity associated with the displayed score, and/or an explanation of the level of pathogenicity associated with various possible scores. In some embodiments, the report display reasons for the calculated pathogenicity score.

In some embodiments the report displays indicators selected from: gene name, gene type, chromosomal location, mutation information (coding change and/or amino acid change), mutation type, form of inheritance, clinical relevance, an associated PubMed ID number, or an associated GenBank Accession No. In some embodiments, the report displays information about a disease known to be associated with the described gene or chromosomal location.

Regarding the variant of unknown clinical significant, in some embodiments, the report displays information selected from: information regarding an amino acid change resulting from the variant, information regarding segregation analysis, information regarding co-occurrence of the variant; information regarding general population frequency of the variant, information regarding amino acid conservation of the codon at which the variant occurs, information regarding SIFT or PolyPhen analysis of the variant, information regarding the protein domain wherein the variant occurs, and information regarding a dbSNP reference. In some embodiments, the report displays citations for relevant peer reviewed articles.

In some embodiments, the report contains recommendations for the end user regarding the information displayed therein. In some embodiments, said recommendations can be chosen from recommendations for further resting of the individual, or the individual's immediate blood relatives.

EXAMPLES

Example 1

This example demonstrates a method of the present disclosure, that is a real-time, rule-based system for the analysis, clinical reporting, and curation of DNA sequence variant data in a CLIA-certified commercial reference laboratory.

Database

A variant database was generated from a collection of data for a plurality of variants. This was done with a Microsoft Access database that is now housed on a SQL server and was adapted to fit the needs through the addition of many forms, subforms, queries and relationships.

Improved Interpretation

The second part of the scoring process was the method of weighing and evaluating the collected data in the database to generate a pathogenicity score (a clinical significance score) for each variant. The score is meant as a tool/indicator to help communicate to a health care provider the assessment of the relative likelihood that the variant is pathogenic (causative of disease symptoms) to the patient who is carrying the variant. Each point of data curated within the database was weighed, with weights determined with machine learning methods.

Scoring Rules

The pathogenicity assessment/scoring process segregated variants into seven ranked categories on a pathogenicity scale, based on the evaluation of the totality of multiple independent types of evidence available for a given variant. Known/certainly pathogenic variants were assigned a score of '7,' known/certainly normal variants were assigned a score of '1,' and variants of unknown significance with no apparent tendency toward benign or pathogenic were assigned a starting value of '4.' Between these points, variants lacking enough data for classification were assigned different scores associated with different degrees of "probable" pathogenicity. This system created consistency between investigators, and it reflected measurable differences in the confidence of a pathogenicity assessment based on accumulated evidence in the medical literature.

The disclosed process of generating a pathogenicity score is exemplified visually, first in a generalized flowchart (FIG. 1), and then in two example flowcharts directed to two different classes of genetic variants (FIG. 2, missense change; FIG. 3, intronic change outside the canonical splice site). These two different classes of variants are those that alter a single amino acid in a protein (termed UAA), and those that do not alter any amino acid in a protein (a UP).

Scoring Validity

Figure 5:
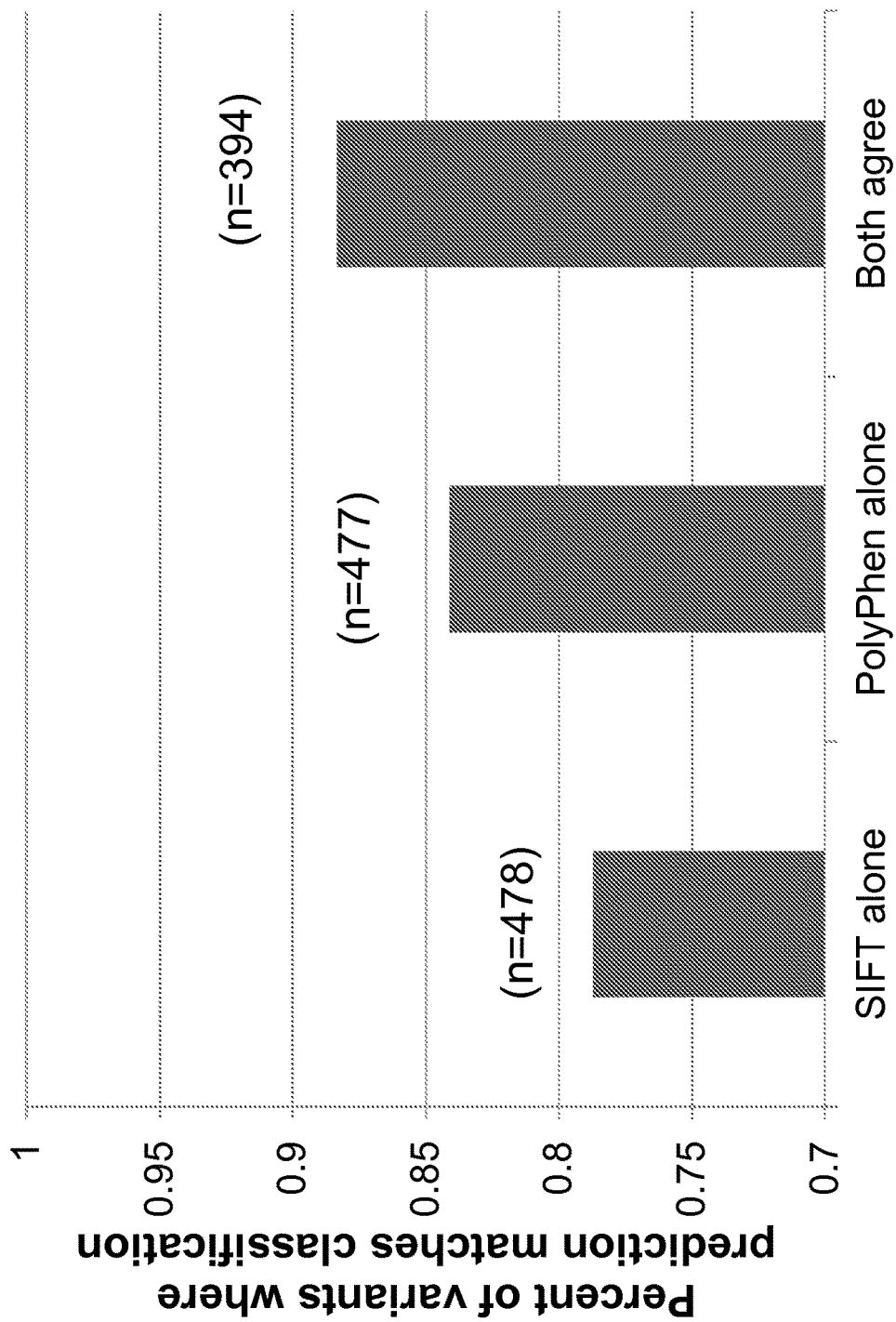
FIG. 5 illustrates the percent of variants where prediction matches classification from SIFT (Sorting Intolerant From Tolerant) and PolyPhen (Polymorphism phenotyping).
Figure 6:
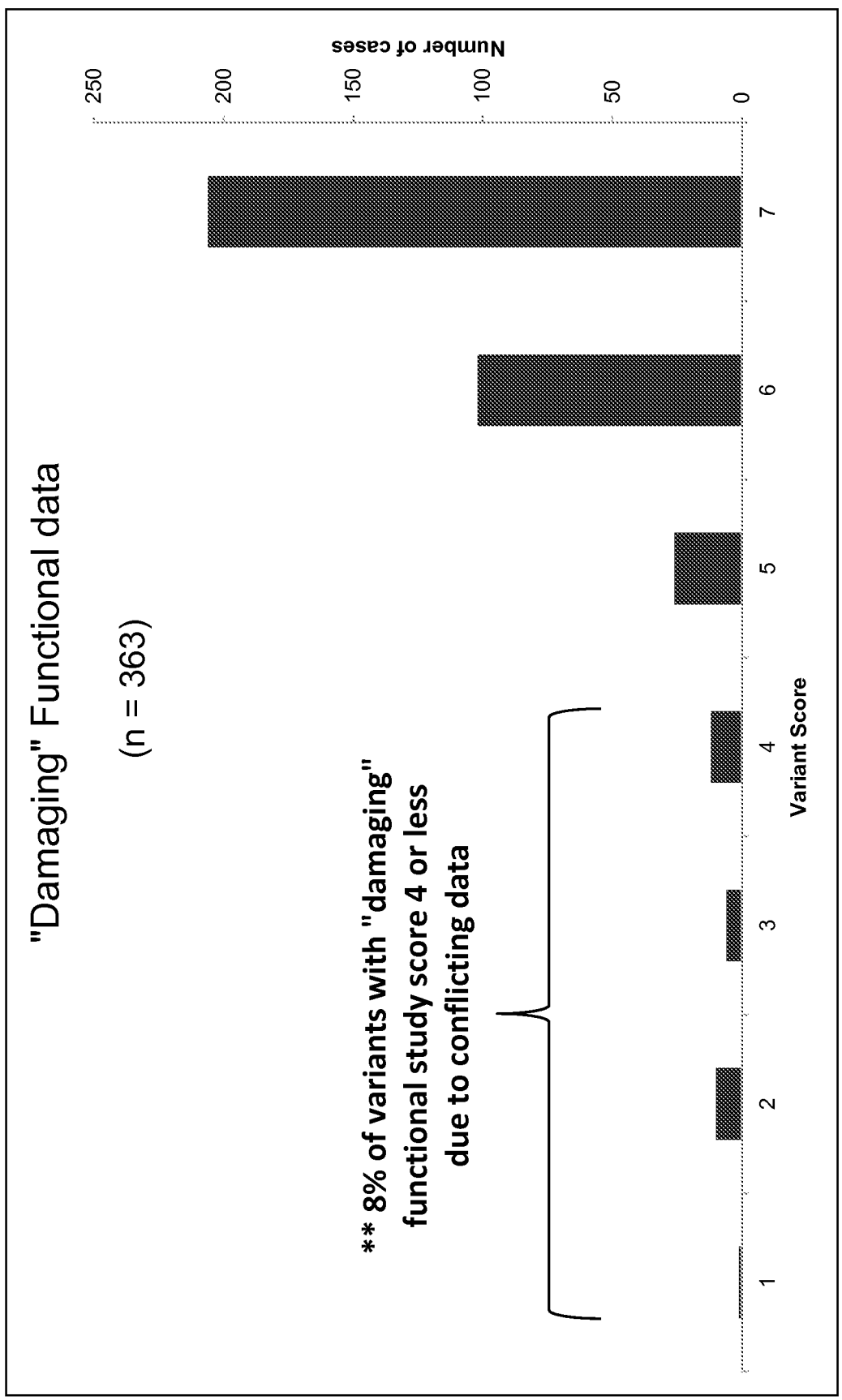
FIG. 6 illustrates the correlation between functional data (with damaging function) of a variant and the clinical significance score determined using the present technology.
Figure 7:
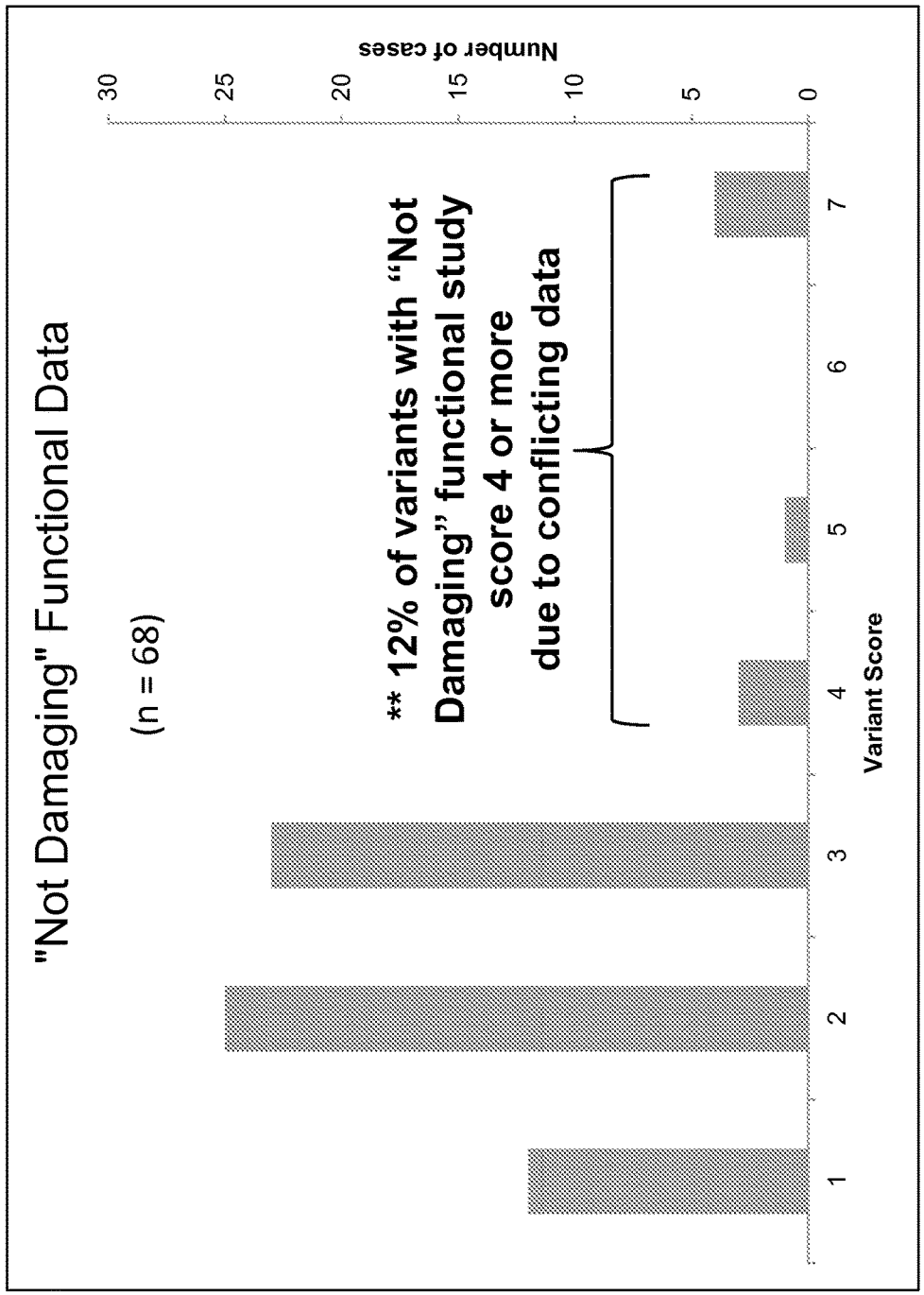
FIG. 7 illustrates the correlation between functional data (without damaging function) of a variant and the clinical significance score determined using the present technology.

The system and method performed 11,771 pathogenicity assessments on 8,813 unique variants focused on neurological, endocrine, and nephrotic genetic disorders. FIG. 5-7 show high concordance of the predicted clinical significance with other parameters. In particular, FIG. 5 demonstrates the percent of variants where prediction by either SIFT alone, PolyPhen alone, or both, matched classification. FIG. 6 exemplifies the distribution of pathogenicity scores of variants with "damaging" function data. Only 8% of variants with "damaging" functional data score 4 or less due to conflicting data. FIG. 7 exemplifies the distribution of pathogenicity scores of variants with "not damaging" function data. 12% of variants with "not damaging" functional data study 4 or more due to conflicting data.

Figure 8:
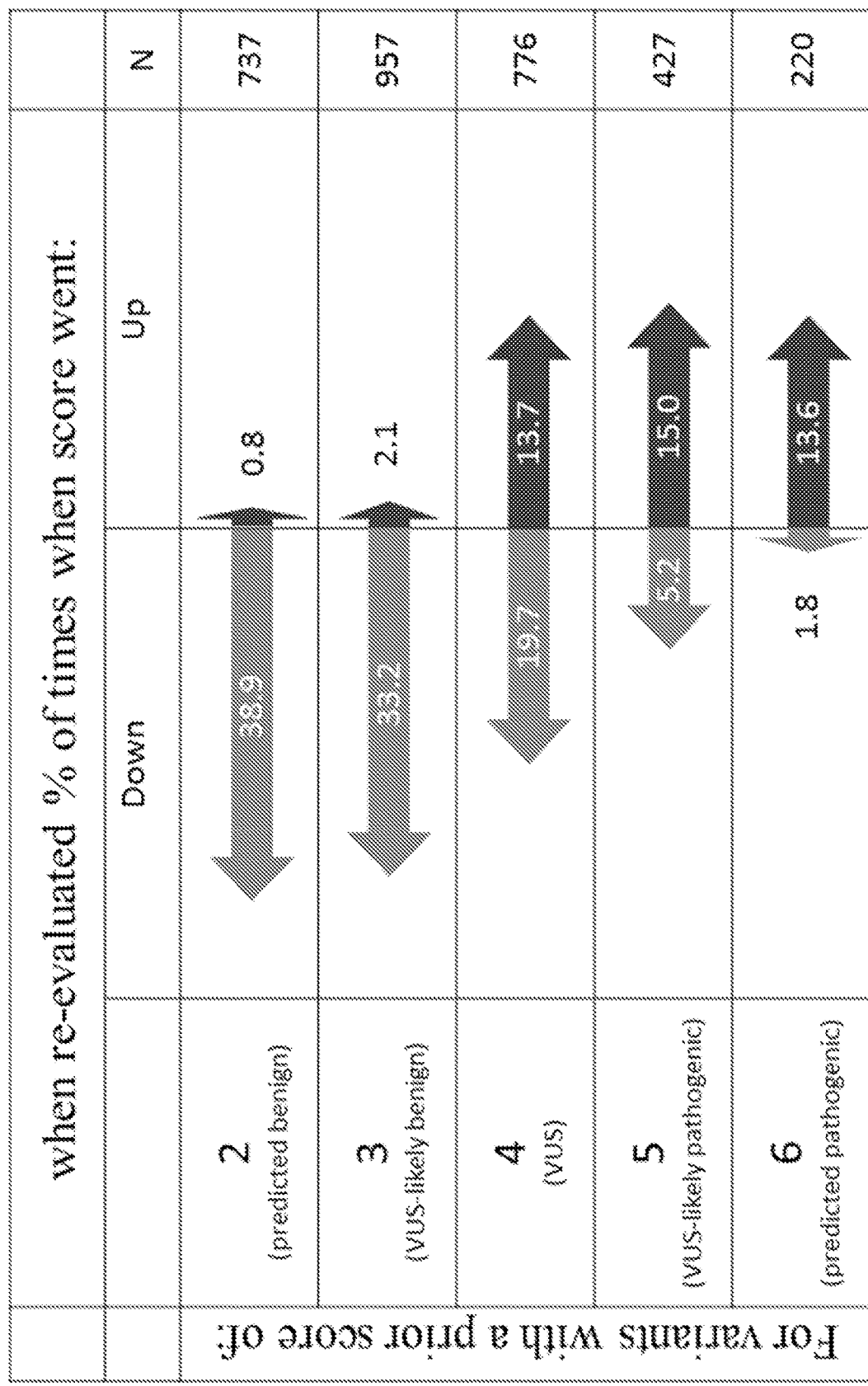
FIG. 8 illustrates how, upon receipt of additional information from the literature, only a small number of variants had their clinical significance score shifted up when their initial clinical significance score was determined to be benign, and only a small number of variants had their score shift down when their initial clinical significance score was determined to be pathogenic.

The effectiveness of the above described scoring system was measured by comparing the stability of variant scoring categories as a function of new data accumulated over time. In a retrospective analysis of the system (FIG. 8), variants scored as a '5' were later downgraded in 5.2% of cases while variants scored as a '6' were downgraded in only 1.8% of cases. Similarly, on the benign end of the scale, variants scoring as 2 or 3 have significantly lower probability of scoring back upward than do variants with higher scores (see FIG. 8). This stability pattern establishes confidence in the scoring categories, supports their inclusion in result reports, and provides evidence that continuous review of variants is needed to assure the quality of the risk interpretation.

Enhanced Reporting

Once the pathogenicity score was assigned, reports for variants that were classified benign and/or pathogenic could be prepared. Text statements were populated according to programming that existed outside the context of this AI process. FIG. 9 exemplifies such a variant report.

The scoring system conforms to ACMG standard rules that require multiple independent lines of evidence to classify a variant as benign or pathogenic. The significance of any single line of evidence is subject to publication bias. In this study, protein functional studies (whether in vitro or in vivo) are more susceptible to bias than other types of evidence. For example, this example identified that 8% of published functional studies on variants have other lines of evidence that directly contradict the functional findings. This illustrates the importance of curating multiple, independent lines of evidence before making a conclusive variant classification.

This example shows that the presently disclosure method is a stable scoring system that conveys confident pathogenicity assessments, effectively communicates risk, and provides useful diagnostic information.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The disclosures illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Other embodiments are set forth within the following claims.

What is claimed is:

1. A method for determining the clinical significance of a genetic variant, comprising determining, for the variant,
    (a) a function score based on known or projected impact of the variant on a biological function of a cell or protein;
    (b) a frequency score based on the frequency of the variant in a population;
    (c) a co-occurrence score based on how the variant co-occurs with a reference variant having known clinical significance relating to a clinical disease or condition;
    (d) a family segregation score based on how the variant segregates with a disease or condition in a family; and
    (e) optionally, a minor evidence score based on information from at least one functional impact prediction algorithm, whether the variant occurs within a critical protein domain, whether the variant would alter a post-translational modification, whether other known pathogenic variants occur within the same codon, and whether the variant is known to occur in at least one patient of a disease or condition;
    aggregating, on a computer, the function score, the frequency score, the co-occurrence score, the family segregation score, and optionally the minor evidence score to generate a clinical significance score indicating the clinical significance of the genetic variant,
        wherein the aggregation comprises summing up the function score, the frequency score, the co-occurrence score, the family segregation score, and optionally the minor evidence score with pre-determined weights or
        wherein the aggregation comprises taking the function score, the frequency score, the co-occurrence score, the family segregation score, and optionally the minor evidence score as inputs in a decision tree, each leaf of the decision tree comprising a value for the clinical significance score; and
    determining that the generated clinical significance score for the variant is above a threshold; and
    wherein an individual identified as having the variant or an immediate blood relative of the individual identified as having the variant is tested for a condition associated with the biological function of the cell or protein, responsive to the determination that the generated clinical significance score for the variant is above the threshold.

2. The method of claim 1, further comprising retrieving, from a database hosted on a computer server, the known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition.

3. The method of claim 1, further comprising determining a curated clinical significance score, wherein the aggregation further takes the curated clinical significance score as an input to generate the clinical significance score.

4. The method of claim 1, wherein the known or projected impact comprises protein activity change or protein expression level change, and wherein a higher impact leads to a higher clinical significance score.

5. The method of claim 4, wherein the protein expression level change is caused by a splicing or translation efficiency change due to the genetic variant.

6. The method of claim 1, wherein the function impact prediction algorithm is selected from SIFT (Sorting Intolerant From Tolerant) and PolyPhen (Polymorphism Phenotyping).

7. The method of claim 1, wherein the minor evidence score is based on information from at least two functional impact prediction algorithms.

8. A method for identifying a potential therapeutic target for treating a disease or condition, comprising
    querying, with a computer, a database comprising genetic variants of a plurality of individuals, each individual annotated with clinically diagnosed diseases or conditions, wherein at least one variant has unknown clinical significance and at least one reference variant has known clinical significance, and wherein for each variant, the database comprises known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition;
    determining a clinical significance score with the method of claim 1, for at least one variant in the database; and
    correlating one of the variants to a disease or condition present in the database, thereby identifying the variant as a potential therapeutic target.

9. A method for predicting whether an individual is likely to suffer from a disease or condition, comprising
    querying, with a computer, a database comprising genetic variants of a plurality of individuals, each individual annotated with clinically diagnosed diseases or conditions, wherein at least one variant has unknown clinical significance and at least one reference variant has known clinical significance, and wherein for each variant, the database comprises known or projected impact of the variant on a biological function of a cell or protein, the frequency of the variant in a population, co-occurrence of the variant with the reference variant relating to a clinical disease or condition, and occurrences of the variant in a family and segregation between the variant and a disease or condition;
    determining a clinical significance score with the method of claim 1, for at least one variant in the database;

correlating one of the variants to a disease or condition present in the database; and identifying an individual possessing the variant as to likely to suffer from the disease or condition.

10. The method of claim 1, further comprising:
generating a visual representation of the aggregation; and
displaying the visual representation on a user device.

11. The method of claim 1, further comprising, responsive to the generated clinical significance score being above a first threshold and below a second threshold, determining, for the variant, a second function score, a second frequency score, a second co-occurrence score, and a second family segregation score, and aggregating the second function score, the second frequency score, the second co-occurrence score, and the second family segregation score to generate a second clinical significance score; wherein at least one of the second function score, the second frequency score, the second co-occurrence score, and the second family segregation score is based on new data accumulated after generating the clinical significance score.

12. The method of claim 1, further comprising excluding a second variant from an output report, responsive to a generated clinical significance score of the second variant being below the threshold.

13. The method of claim 1, wherein determining each of the co-occurrence score and the family segregation score comprise retrieving, by the computer, from an integrated database comprising a plurality of variants and associated patients, corresponding co-occurrence or family segregation data for the variant.

* * * * *